United States Patent
Shalyt et al.

(10) Patent No.: US 6,890,758 B2
(45) Date of Patent: May 10, 2005

(54) MEASUREMENT OF COMPLEXING AGENT CONCENTRATION IN AN ELECTROLESS PLATING BATH

(75) Inventors: Eugene Shalyt, Washington Township, NJ (US); Michael Pavlov, Fairlawn, NJ (US); Peter Bratin, Flushing, NY (US); Alex Kogan, Carlstadt, NJ (US); Michael James Perpich, Hackensack, NJ (US)

(73) Assignee: ECI Technology, Inc., East Rutherford, NJ (US)

(*) Notice: Subject to any disclaimer, the term of this patent is extended or adjusted under 35 U.S.C. 154(b) by 123 days.

(21) Appl. No.: 10/461,652

(22) Filed: Jun. 13, 2003

(65) Prior Publication Data

US 2004/0253740 A1 Dec. 16, 2004

(51) Int. Cl.[7] .............................................. G01N 31/16
(52) U.S. Cl. .................. 436/163; 436/51; 436/111; 436/112; 436/124; 436/125; 436/128; 436/150
(58) Field of Search .......................... 436/163, 50, 111, 436/112, 124, 125, 128, 150; 422/75–77, 82.03; 205/778.5, 788.5, 794

(56) References Cited

U.S. PATENT DOCUMENTS

| | | | | |
|---|---|---|---|---|
| 4,541,902 A | * | 9/1985 | Kinoshita et al. | ............ 205/786 |
| 6,673,226 B1 | * | 1/2004 | Bratin et al. | ................... 205/81 |
| 6,709,561 B1 | * | 3/2004 | Pavlov et al. | .................. 205/81 |

OTHER PUBLICATIONS

Efstathiou and Hadjiioannou, Analytica Chim. Acta *109*, 319 (1979).

* cited by examiner

Primary Examiner—Jan M. Ludlow
(74) Attorney, Agent, or Firm—D. Morgan Tench

(57) ABSTRACT

The concentration of citrate complexing agent in an electroless cobalt or nickel plating bath is determined by titrating a sample of the electroless plating bath containing a small concentration of free fluoride ion with a standard lanthanum nitrate solution. During the titration, $La^{3+}$ ion first reacts preferentially with the citrate complexing agent and then with fluoride ion, which reduces the free fluoride ion concentration. The endpoint for the titration is indicated by a substantial decrease in the free fluoride ion concentration, which is detected via a fluoride ion specific electrode (ISE). The method can be used for analysis of other complexing agents.

23 Claims, 1 Drawing Sheet

MEASUREMENT OF COMPLEXING AGENT CONCENTRATION IN AN ELECTROLESS PLATING BATH

CROSS-REFERENCE TO RELATED APPLICATIONS

This application is related to U.S. patent application Ser. No. 10/288,989 (filed Nov. 6, 2002) to Pavlov et al., which is assigned to the same assignee. The teachings of this patent application are incorporated herein by reference.

BACKGROUND OF THE INVENTION

1. Field of the Invention

This invention is concerned with analysis of complexing agents in electroless plating baths as a means of providing control over the deposit properties.

2. Description of the Related Art

Plating baths are widely used by the electronics industry to deposit a variety of metals (copper, nickel and gold, for example) on various parts, including circuit boards, semiconductor chips, and device packages. Both electroplating baths and electroless plating baths are employed. For electroplating, the part and a counter electrode are brought into contact with the electroplating bath containing ions of an electrodepositable metal, and the metal is electrodeposited by applying a negative potential to the part relative to the counter electrode. For electroless plating, the bath also contains a reducing agent which, in the presence of a catalyst, chemically reduces the metal ions to form a deposit of the metal. Since the deposited metal itself may serve as the catalyst, the electroless deposition, once initiated, proceeds without the need for an externally applied potential.

The electronics industry is transitioning from aluminum to copper as the basic metallization for semiconductor integrated circuits (IC's) in order to increase device switching speed and enhance electromigration resistance. The leading technology for fabricating copper IC chips is the "Damascene" process (see, e.g., P. C. Andricacos, Electrochem. Soc. Interface, Spring 1999, p.32; U.S. Pat. No. 4,789,648 to Chow et al.; U.S. Pat. No. 5,209,817 to Ahmad et al.), which depends on copper electroplating to provide complete filling of the fine features involved.

In the Damascene process, as currently practiced, vias and trenches are etched in the chip's dielectric material, which is typically silicon dioxide, although materials with lower dielectric constants are under development. A barrier layer, e.g., titanium nitride (TiN), tantalum nitride (TaN) or tungsten nitride ($WN_x$), is deposited on the sidewalls and bottoms of the trenches and vias, typically by reactive sputtering, to prevent Cu migration into the dielectric material and degradation of the device performance. Over the barrier layer, a thin copper seed layer is deposited, typically by sputtering, to provide enhanced conductivity and good adhesion. Copper is then electrodeposited into the trenches and vias. Copper deposited on the outer surface, i.e., outside of the trenches and vias, is removed by chemical mechanical polishing (CMP). A capping or cladding layer (e.g., TiN, TaN or $WN_x$) is applied to the exposed copper circuitry to suppress oxidation and migration of the copper. The "Dual Damascene" process involves deposition in both trenches and vias at the same time. In this document, the term "Damascene" also encompasses the "Dual Damascene" process.

Damascene barrier layers based on electrolessly deposited cobalt and nickel are currently under investigation [e.g., Kohn et al., Mater. Sci. Eng. A302, 18 (2001)]. Such metallic materials have higher electrical conductivities compared to metal nitride barrier materials, which enables copper to be electrodeposited directly on the barrier layer without the use of a copper seed layer. Higher barrier layer conductivity also reduces the overall resistance for circuit traces of a given cross-sectional area. In addition, electroless deposition provides highly conformal coatings, even within ultra-fine trenches and vias, so that the overall coating thickness can be minimized. Electroless cobalt and nickel baths being investigated for Damascene barrier deposition typically also contain a refractory metal (e.g., tungsten, molybdenum or rhenium), which co-deposits with the cobalt or nickel and increases the maximum temperature at which effective barrier properties are retained.

For electroless cobalt and nickel baths, hypophosphite ($H_2PO_2^-$) is typically used as the reducing agent, which introduces phosphorus into the deposit. The codeposited phosphorus reduces the deposit grain size and crystallinity (compared to electrodeposits), which tends to improve the deposit barrier properties. Alternative reducing agents include the boranes, dimethylamineborane (DMAB), for example. Use of a borane reducing agent introduces boron into the deposit. A typical bath for electroless deposition of Damascene barrier layers comprises 0.1 M cobalt chloride or sulfate, 0.2 M sodium hypophosphite, 0.03 M sodium tungstate, 0.5 M sodium citrate, 0.5 M boric acid, and a small amount of a surfactant. Such Co(W, P) baths typically operate at about pH 9 and a temperature of 85°–95° C., and may also contain organic additives.

For electroless deposition of cobalt and nickel on dielectric materials, such as silicon oxide, or on metals that are not sufficiently catalytic for the electroless process, such as copper, a seed layer of a catalytic metal is generally employed. Typically, catalytic palladium is deposited by immersion of the part in an acidic activator solution containing palladium chloride and fluoride ion. The fluoride ion tends to cause dissolution of surface oxides on the substrate so that a displacement layer of palladium is formed. Alternatively, a seed layer of the electrolessly deposited metal, cobalt or nickel, may be applied by sputtering.

Recently, direct deposition of capping layers of Co(W, P) on Damascene copper circuits was reported [T. Itabashi, N. Nakano and H. Akahoshi, Proc. IITC 2002, p. 285–287] for a Co(W, P) bath employing two reducing agents. In this case, electroless deposition is initiated by the more active reducing agent (DMBA), which is present at a relatively low concentration. As the DMBA reducing agent becomes depleted at the part surface, electroless deposition is sustained by the less active reducing agent (hypophosphite), which provides better deposit properties.

Close control of the concentrations of the constituents of electroless plating baths is necessary to provide acceptable deposit properties. Some constituents can be detected by standard analytical techniques whereas specialized methods are needed to measure the concentrations of other constituents. A method for measuring the concentration of reducing agents in electroless plating baths, based on metal electrodeposition rate measurements, is described in a U.S. patent application Ser. No. 10/288,989 to Pavlov et al. (filed Nov. 6, 2002).

Measurement of the concentrations of complexing agents in electroless plating baths is complicated by the presence of reducing agents and buffering agents. Reducing agents tend to interfere with analyses based on redox reactions, whereas buffering agents tend to interfere with acid-base titrations. In addition, complexing agents employed in electroless plating baths are generally weak complexing agents (citrate ion, for example), whose concentrations cannot be readily measured by complexometric titrations. Thus, the conventional approach of determining the concentration of "free" complexing agent by titration with a metal salt solution, and determining the concentration of complexed species by a separate analysis, cannot be used for the relatively weak complexing agents employed in electroless plating baths. Such two-part analyses are undesirable in any case since measurement errors for the separate analyses are multiplied. A method is needed for accurately measuring the concentration of complexing agents, such as citrate ion, in electroless plating baths.

Analysis of various anionic species (sulfate, chromate, molybdate, tungstate, oxalate, phosphate, pyrophosphate and hexacyanoferrate) by addition of fluoride and chloride ions to the unknown solution and titration with lead nitrate is described in the prior art literature [C. E. Efstathiou and P. Hadjiioannou, Analytica Chimica Acta 109, 319 (1979)]. In this case, $Pb^{2+}$ ions in the titrant react with the anion of interest until it is consumed, and then precipitate PbClF by reaction with the added chloride and fluoride ions. The endpoint for the titration is signaled by a decrease in fluoride ion concentration, which is detected via a fluoride ion specific electrode. In this case, addition of an organic solvent (acetone, ethanol or propan-2-ol, for example) to the unknown solution enhances PbClF precipitation and sharpens the endpoint.

This prior art method has not been applied to analysis of complexing agents in electroless plating baths but would have significant disadvantages for that application. In particular, lead is a toxic metal so that use of $Pb^{2+}$ ion as a reagent creates safety and environmental issues. Another disadvantage is that the PbClF precipitate is difficult to remove from reaction vessels and can significantly increase the time needed for rinsing between analyses, and/or introduce measurement errors via cross-contamination. In addition, organic solvents used to enhance the precipitation reaction and sharpen the titration endpoint are also objectionable from safety and environmental standpoints.

SUMMARY OF THE INVENTION

This invention provides a method for determining the concentration of a complexing agent in an electroless plating bath. In this method, a test solution comprising a sample of the electroless plating bath and a small concentration of free fluoride ion is titrated with a titrant solution containing complexing metal ions ($La^{3+}$ ions, for example) of a type tending to form a relatively strong complex with the complexing agent (citrate ion, for example). As the complexing metal ions are added to the test solution, they preferentially react the complexing agent until it is consumed, and then react with the free fluoride ions, which reduces the free fluoride ion concentration in the test solution. The endpoint for the titration is indicated by a substantial decrease in the free fluoride ion concentration, which is detected via a fluoride ion specific electrode (ISE). For a complexing agent that complexes the complexing metal ions substantially more strongly than the ions of the electrolessly deposited metal, the method of the present invention yields the total concentration of the complexing agent.

The method of the present invention is particularly useful for analyzing the concentration of the citrate complexing agent typically employed in electroless cobalt and nickel baths of the type used for depositing barrier and capping layers for Damascene copper circuits. The analysis can be performed rapidly and enables close control of the complexing agent concentration needed to ensure acceptable metal deposits. Only one analysis is required so that measurement errors are minimized. No hazardous reagents are required for the analysis and no precipitates are involved, which facilitates rinsing between analyses and minimizes cross-contamination.

Further features and advantages of the invention will be apparent to those skilled in the art from the following detailed description, taken together with the accompanying drawings.

BRIEF DESCRIPTION OF THE DRAWINGS

FIG. 2 shows the mathematical differentials of the curves from FIG. 1 vs. volume of 0.1 M $La(NO_3)_3$ titrant solution added to the test solutions containing 50, 60 and 70 g/L sodium citrate complexing agent.

DETAILED DESCRIPTION OF THE INVENTION

Figure 1:
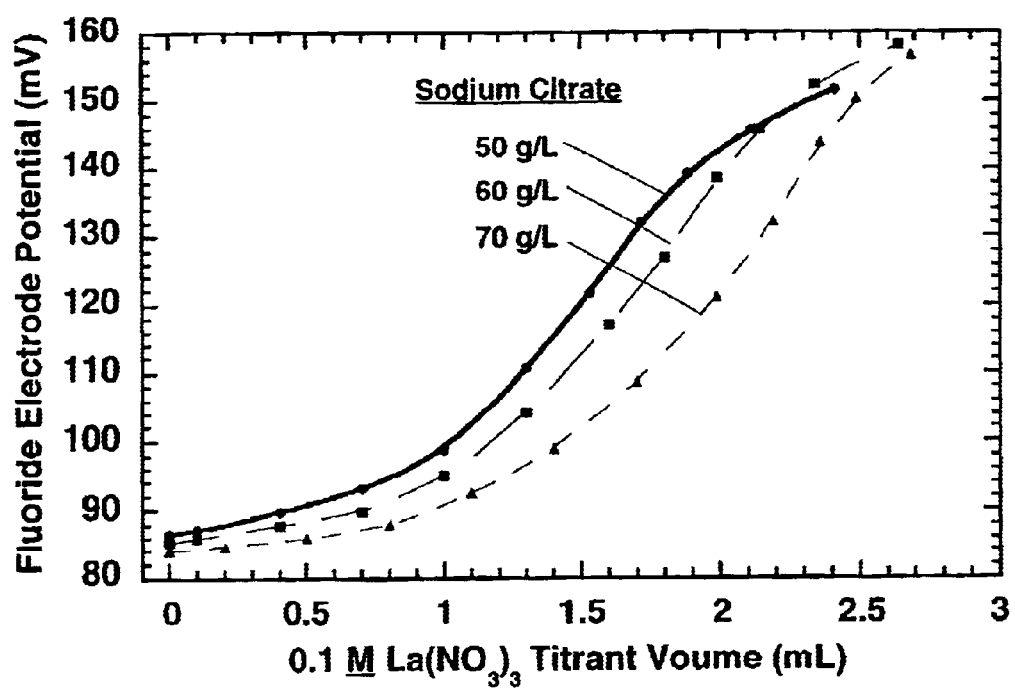
FIG. 1 shows potentiometric titration curves of fluoride ISE potential vs. volume of 0.1 M $La(NO_3)_3$ titrant solution added to test solutions containing 50, 60 and 70 g/L sodium citrate complexing agent.

Technical terms used in this document are generally known to those skilled in the art. A "titration" to determine the concentration of an "analyte" species in a test solution involves standard additions (to the test solution) of a titrant solution containing a predetermined (known) concentration of a "titrant" species, which reacts with the analyte species. The concentration of the analyte is determined from the volume of the titrant solution required to reach the "equivalence point" for the titration, which corresponds to substantially complete consumption of the analyte in the test solution by reaction with the titrant. Ideally, the equivalence point is the "endpoint" for the titration but in practice an appreciable excess of titrant may be required to produce a detectible endpoint effect. The term "standard addition" generally means addition of a known volume of a first solution to a known volume of a second solution, and the "volume ratio" is the volume of the first solution divided by the total volume of the solution resulting from addition of the first solution to the second solution. The symbol "M" means molar concentration. Data are conventionally handled as curves or plots but data may also be tabulated and used directly, especially by a computer, and the terms "curve" or "plot" include tabulated data.

This invention provides a method for determining the concentration of a complexing agent in an electroless plating bath. In this method, a test solution comprising a sample of the electroless plating bath and a small concentration of free fluoride ion is titrated with a titrant solution containing a predetermined concentration of complexing metal ions of a type tending to form a relatively strong complex with the complexing agent. As the complexing metal ions are added to the test solution, they preferentially react with the complexing agent until it is consumed, and then react with the fluoride ions. The endpoint for the titration is indicated by a substantial decrease in the free fluoride ion concentration in the test solution. The concentration of the complexing agent in the plating bath is calculated from the concentration of the complexing metal ions in the titrant solution, and the volume ratio of the titrant solution required to reach the titration end point. For a complexing agent that complexes the complexing metal ions more strongly than the ions of the electrolessly deposited metal, the method of the present invention yields the total complexing agent concentration. The endpoint for the titration is determined by monitoring the concentration of free fluoride ion in the test solution using a fluoride ion specific electrode. Such electrodes, which exhibit a potential proportional to the free fluoride ion concentration, are available commercially.

A preferred complexing metal ion is lanthanium ion ($La^{3+}$), which tends to form exceptionally strong anion complexes compared to ions of other metals. The $La^{3+}$ ion also has low electroactivity, and provides a sharp endpoint with the fluoride ion specific electrode since $LaF_3$ is highly insoluble. Alternative complexing metal ions that could be used include $Fe^{3+}$, $Hg^{2+}$ and $Ce^{4+}$ ions. The counter ion used with the complexing metal ion is preferably non-complexing or only weakly complexing so that interference with the complexing agent analysis is minimized. Preferred complexing metal counter ions include nitrate ($NO_3^-$) and perchlorate ($ClO_3^-$), for example, but other counter ions may be used. The complexing metal ion is present in the titrant solution at a predetermined (known) concentration, which can be varied widely. The complexing metal ion concentration is preferably chosen to provide good sensitivity to the complexing agent while avoiding excessive titrant volumes that would be difficult to handle. A typical titrant solution for electroless cobalt and nickel baths is 0.1 M $La(NO_3)_3$ dissolved in de-ionized water. Suitable concentrations for the complexing metal ion concentration could range from 0.01 to 1.0 M, depending on various analytical considerations, including the concentration of the complexing agent in the electroless plating bath.

Fluoride ion is used as the titration endpoint indicator since it is a very weak complexing agent that substantially complexes with the complexing metal ion only after the complexing agent used in the plating bath is consumed. The counter ion used with fluoride ion is preferably a poor complexing agent compared to the complexing metal ion so that interference with the complexing agent analysis is minimized. Suitable fluoride counter ions include the alkali metal ions ($Li^+$, $Na^+$, $K^+$, $Rb^+$ and $Cs^+$) but other counter ions may be used. Typically, fluoride is added to the test solution as NaF salt dissolved in de-ionized water.

The concentration of free fluoride ion in the test solution is preferably a predetermined value providing optimum titration endpoint sharpness and good correspondence between the equivalence point and the endpoint. The predetermined free fluoride concentration should be large enough to be readily detectable by a fluoride ion specific electrode, but should not be so large that small changes in free fluoride ion concentration do not produce a readily measurable change in ISE potential. The predetermined free fluoride concentration is preferably 0.5 to 500 mg/L. For relatively large free fluoride concentrations, it may be necessary to correct the titrant volume for the difference between the equivalence point and the endpoint.

The substantial decrease in free fluoride concentration corresponding to the titration endpoint can be rendered more apparent and precisely defined by differentiating potentiometric titration curves of fluoride ion specific electrode potential vs. volume of added titrant solution. The first-derivative curve exhibits a peak corresponding to the maximum rate of change in electrode potential with titrant volume, which can be used as the titration endpoint. The location of the peak in the first-derivative curve can be more exactly determined by taking the second derivative, for which the peak value is zero. These mathematical manipulations, including extrapolations between data points or to a zero-value second derivative, can readily be handled via a computer. In some cases, a calibration curve with only two or three points may be used.

The method of the present invention is particularly useful for measuring the concentration of complexing agents in electroless cobalt and nickel baths, including those from which other metals (tungsten, molybdenum or rhenium, for example) are co-deposited. Such baths typically employ citrate (added as sodium citrate) as the primary complexing agent but the method may also be used to determine the concentrations of other complexing agents, including lactate, succinate, hydroxyacetate, aminoacetate, malonate, ethylenediamine, and ethylenediamine tetraacetate. The method could also be used to analyze complexing agents in electroless baths for plating other metals, copper, gold, palladium and platinum, for example.

To minimize interference with the complexing agent analysis, substantial variations in the concentrations of other constituents of the plating bath sample should be avoided. For example, variations in pH and cobalt ion concentration in electroless cobalt baths have been found to affect the citrate analysis results. Preferably, the pH and cobalt ion concentrations in the bath are maintained at substantially constant values with respect to the citrate analysis. Alternatively, the pH and cobalt ion concentrations in the plating bath sample may be adjusted prior to the citrate analysis. Another approach to maintaining a constant pH for the complexing agent analysis is to buffer the test solution, typically by addition of a buffer solution. For an electroless cobalt bath with a target pH value around 9, a suitable buffer solution is 0.1 M $NH_4Cl$ adjusted to the target pH by addition of $NH_4OH$ solution. A variety of buffer solutions may be used. Similar approaches for minimizing the effects of variations in the concentrations of interfering species can be used for analysis of other plating baths and other complexing agents.

DESCRIPTION OF A PREFERRED EMBODIMENT

In a preferred embodiment of the present invention, the concentration of citrate complexing agent ($C_6H_5O_7^{3+}$) in an electroless cobalt or nickel plating bath is determined by titrating a sample of the electroless plating bath containing a small concentration of NaF (0.5–500 mg/L) with a 0.1 M $La(NO_3)_3$ titrant solution. As the titrant solution is added to the test solution (plating bath sample containing free fluoride ion), $La(NO_3)_3$ reacts with sodium citrate ($Na_3C_6H_5O_7$) to form lanthanum citrate ($LaC_6H_5O_7$) and sodium nitrate ($NaNO_3$), according to the equation:

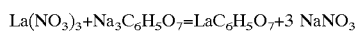

$$La(NO_3)_3 + Na_3C_6H_5O_7 = LaC_6H_5O_7 + 3\ NaNO_3$$

After the equivalence point is reached, lanthanum nitrate begins reacting with sodium fluoride (NaF) to form lanthanum fluoride ($LaF_3$), according to the equation:

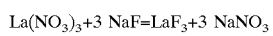

$$La(NO_3)_3 + 3\ NaF = LaF_3 + 3\ NaNO_3$$

which causes the free fluoride concentration to decrease since fluoride is much more strongly complexed in the $LaF_3$ species than in the NaF species. The decrease in free fluoride concentration, which signals the endpoint for the titration, is detected via a fluoride ion specific electrode. The concentration of citrate ion in the electroless plating bath is calculated from the concentration of the $La(NO_3)_3$ in the titrant solution and the volume ratio of the titrant solution required to reach the titration end point.

For the complexing agent analysis of the present invention, the concentrations of other constituents in the electroless plating bath are preferably maintained within the ranges recommended by the bath supplier so as to ensure minimal interference from other bath species. During the titration, the test solution should be stirred to ensure substantially complete reaction between the complexing metal ions and the complexing agent (and free fluoride ion). Solution stirring can be provided by any suitable means, including hand stirring, motorized impellor stirring, magnetic stirring, and ultrasonic stirring. After each standard addition, sufficient time should be allowed for stirring to provide a homogeneous solution. The titration is typically performed at ambient temperature but temperature is not a critical parameter.

A preferred approach for minimizing the effects of variations in the pH of the plating bath on the complexing agent analysis is to utilize a buffered test solution, which may be prepared by diluting the plating bath sample with deionized water and adding a buffer solution. The pH of the buffer solution is preferably the same as the target pH of the plating bath. For analysis of citrate in electroless cobalt plating baths operating at pH 9, a suitable buffer solution is 0.1 M $NH_4Cl$ adjusted to the target pH by addition of $NH_4OH$ solution. Suitable results for such citrate analysis are obtained with a test solution prepared by adding 0.5–1.0 mL of the plating bath sample to 50–100 mL of deionized water, and adding about 5 mL of the buffer solution (and 0.1 mL of 0.1 M NaF solution).

The efficacy of the present invention was demonstrated via analysis of an electroless cobalt bath containing 0.1 M cobalt sulfate, 0.2 M sodium hypophosphite, 0.03 M sodium tungstate, 0.5 M boric acid, a small amount of a surfactant, and various concentrations of sodium citrate. Before titration with 0.1 M $La(NO_3)_3$ titrant solution, 14 mg/L sodium fluoride was added to the plating bath sample (1.0 mL volume). A motorized stirrer was used to homogenize the solution. Titrations were performed under computer control.

FIG. 1 shows potentiometric titration curves of fluoride ISE potential vs. volume of 0.1 M $La(NO_3)_3$ titrant solution added to test solutions containing 50, 60 and 70 g/L sodium citrate complexing agent. As the concentration of sodium citrate in the test solution increases, it is evident that a greater volume of titrant solution is required to produce a substantial increase in the potential of the fluoride ion specific electrode.

FIG. 2 shows the mathematical differentials of the curves from FIG. 1 vs. volume of 0.1 M $La(NO_3)_3$ titrant solution added to the test solutions containing 50, 60 and 70 g/L sodium citrate complexing agent. The peaks in the differential curves correspond to maximum slope in the potentiometric titration curves and provide a reliable endpoint for the citrate titration.

Table 1 shows citrate titration results for series of ten measurements on electroless Co(W, P) baths made up to contain low (50 mg/L), standard (60 mg/L) and high (70 mg/L) concentrations of sodium citrate complexing agent. The relative standard deviations were 1.18%, 0.88% and 0.38%, respectively.

TABLE 1

Citrate Analysis Results for Electroless Co(W, P) Plating Baths

|  |  |  |
| --- | --- | --- |
| 51.10 | 59.87 | 69.96 |
| 49.96 | 60.82 | 69.96 |
| 49.64 | 60.24 | 70.33 |
| 48.75 | 59.10 | 70.09 |
| 50.09 | 60.24 | 69.46 |
| 49.96 | 60.88 | 69.96 |
| 49.96 | 60.24 | 69.96 |
| 49.96 | 59.98 | 70.05 |
| 50.42 | 59.87 | 69.48 |
| 50.17 | 59.63 | 69.96 |
| Averages 50.00 | 60.09 | 69.92 |
| Actuals 50.00 | 60.00 | 70.00 |
| Standard Deviations 1.18% | 0.88% | 0.38% |

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method for determining the concentration of a complexing agent in an electroless plating bath, comprising the steps of:
   providing a test solution comprising a sample of the electroless plating bath and a predetermined concentration of fluoride ion;
   titrating the test solution with a titrant solution comprising a predetermined concentration of a complexing metal ion;
   detecting a substantial decrease in the concentration of fluoride ion in the test solution via a fluoride ion specific electrode; and
   calculating the concentration of the complexing agent in the electroless plating bath from the volume ratio of the test solution required to produce the substantial decrease in the concentration of the fluoride ion in the test solution.

2. The method of claim 1, wherein the electroless plating bath is of a type used to deposit a metal selected from the group consisting of cobalt, nickel, molybdenum, tungsten, rhenium, copper, gold, palladium, platinum, and alloys thereof.

3. The method of claim 1, wherein the complexing agent is selected from the group consisting of citrate, lactate, succinate, hydroxyacetate, aminoacetate, malonate, ethylenediamine, and ethylenediamine tetraacetate.

4. The method of claim 1, wherein the predetermined concentration of fluoride ion has a value in the 0.5 to 500 mg/L range.

5. The method of claim 1, wherein the predetermined concentration of the complexing metal ion is from 0.01 to 1.0 M.

6. The method of claim 1, wherein the complexing metal ion is selected from the group consisting of $La^{3+}$, $Fe^{3+}$, $Hg^{2+}$ and $Ce^{4+}$ ions.

7. The method of claim 1, wherein said step of detecting a substantial decrease in the concentration of fluoride ion in the test solution includes the step of generating a titration curve of fluoride ion specific electrode potential versus volume of added titrant solution.

8. The method of claim 7, wherein said step of detecting a substantial decrease in the concentration of fluoride ion in the test solution further includes the step of taking the first derivative of the titration curve.

9. The method of claim 7, wherein said step of detecting a substantial decrease in the concentration of fluoride ion in the test solution further includes the step of taking the second derivative of the titration curve.

10. The method of claim 1, wherein the test solution further comprises a buffer solution.

11. A method for determining the concentration of a complexing agent in an electroless plating bath, comprising the steps of:
   providing a test solution comprising a sample of the electroless plating bath and a predetermined concentration of fluoride ion;
   titrating the test solution with a titrant solution comprising a predetermined concentration of $La^{3+}$ ion;
   detecting a substantial decrease in the concentration of fluoride ion in the test solution via a fluoride ion specific electrode; and
   calculating the concentration of the complexing agent in the electroless plating bath from the volume ratio of the test solution required to produce the substantial decrease in the concentration of the fluoride ion in the test solution.

12. The method of claim 1, wherein the electroless plating bath is of a type used to deposit a metal selected from the group consisting of cobalt, nickel, molybdenum, tungsten, rhenium, copper, gold, palladium, platinum, and alloys thereof.

13. The method of claim 11, wherein the complexing agent is selected from the group consisting of citrate, lactate, succinate, hydroxyacetate, aminoacetate, malonate, ethylenediamine, and ethylenediamine tetraacetate.

14. The method of claim 11, wherein the predetermined concentration of fluoride ion has a value in the 0.5 to 500 mg/L range.

15. The method of claim 11, wherein the predetermined concentration of the of $La^{3+}$ ion is from 0.01 to 1.0 M.

16. The method of claim 11, wherein said step of detecting a substantial decrease in the concentration of fluoride ion in the test solution includes the step of generating a titration curve of fluoride ion specific electrode potential versus volume of added titrant solution.

17. The method of claim 16, wherein said step of detecting a substantial decrease in the concentration of fluoride ion in the test solution further includes the step of taking the first derivative of the titration curve.

18. The method of claim 16, wherein said step of detecting a substantial decrease in the concentration of fluoride ion in the test solution further includes the step of taking the second derivative of the titration curve.

19. The method of claim 11, wherein the test solution further comprises a buffer solution.

20. A method for determining the concentration of citrate complexing agent in an electroless plating bath, comprising the steps of:
   providing a test solution comprising a sample of the electroless plating bath and a predetermined concentration of fluoride ion;
   titrating the test solution with a titrant solution comprising a predetermined concentration of $La^{3+}$ ion;
   detecting a substantial decrease in the concentration of fluoride ion in the test solution via a fluoride ion specific electrode; and
   calculating the concentration of the citrate complexing agent in the electroless plating bath from the volume ratio of the test solution required to produce the substantial decrease in the concentration of the fluoride ion in the test solution.

21. The method of claim 20, wherein the electroless plating bath is of a type used to deposit a metal selected from the group consisting of cobalt, nickel, molybdenum, tungsten, rhenium, copper, gold, palladium, platinum, and alloys thereof.

22. A method for determining the concentration of citrate complexing agent in an electroless cobalt or nickel plating bath, comprising the steps of:
   providing a test solution comprising a sample of the cobalt or nickel electroless plating bath and a predetermined concentration of fluoride ion;
   titrating the test solution with a titrant solution comprising a predetermined concentration of $La^{3+}$ ion;
   detecting a substantial decrease in the concentration of fluoride ion in the test solution via a fluoride ion specific electrode; and
   calculating the concentration of the citrate complexing agent in the electroless plating bath from the volume ratio of the test solution required to produce the substantial decrease in the concentration of the fluoride ion in the test solution.

23. A method for determining the concentration of citrate complexing agent in an electroless cobalt or nickel plating bath, comprising the steps of:
   providing a test solution comprising a sample of the cobalt or nickel electroless plating bath, a buffer solution, and a predetermined concentration of fluoride ion;
   titrating the test solution with a titrant solution comprising a predetermined concentration of $La^{3+}$ ion;
   detecting a substantial decrease in the concentration of fluoride ion in the test solution via a fluoride ion specific electrode; and
   calculating the concentration of the citrate complexing agent in the electroless plating bath from the volume ratio of the test solution required to produce the substantial decrease in the concentration of the fluoride ion in the test solution.

* * * * *